United States Patent [19]

Leonard

[11] Patent Number: 4,634,378
[45] Date of Patent: Jan. 6, 1987

[54] DENTAL DRILL

[75] Inventor: Henri Leonard, Besancon, France

[73] Assignee: Micro-Mega, Besancon, France

[21] Appl. No.: 531,445

[22] Filed: Sep. 12, 1983

[30] Foreign Application Priority Data

Dec. 10, 1982 [FR] France .................................. 82 20903

[51] Int. Cl.$^4$ ............................................... A01C 5/02
[52] U.S. Cl. .................................................. 433/102
[58] Field of Search .......................... 433/65, 102, 165

[56] References Cited

U.S. PATENT DOCUMENTS 1,307,446  6/1919  Kerr ..................................... 433/102
3,579,830 10/1969  Morel .................................. 433/102

Primary Examiner—Robert Peshock
Attorney, Agent, or Firm—Robert E. Burns; Emmanuel J. Lobato; Bruce L. Adams

[57] ABSTRACT

The invention relates to a dental drill.

According to the invention, the drill has a triple helicoidal flute and progressive pitch, the free spaces between the cutting lips increasing from the tip (3) toward the shank (1) of the drill.

Application: dental apparatus.

2 Claims, 4 Drawing Figures

U.S. Patent  Jan. 6, 1987  4,634,378
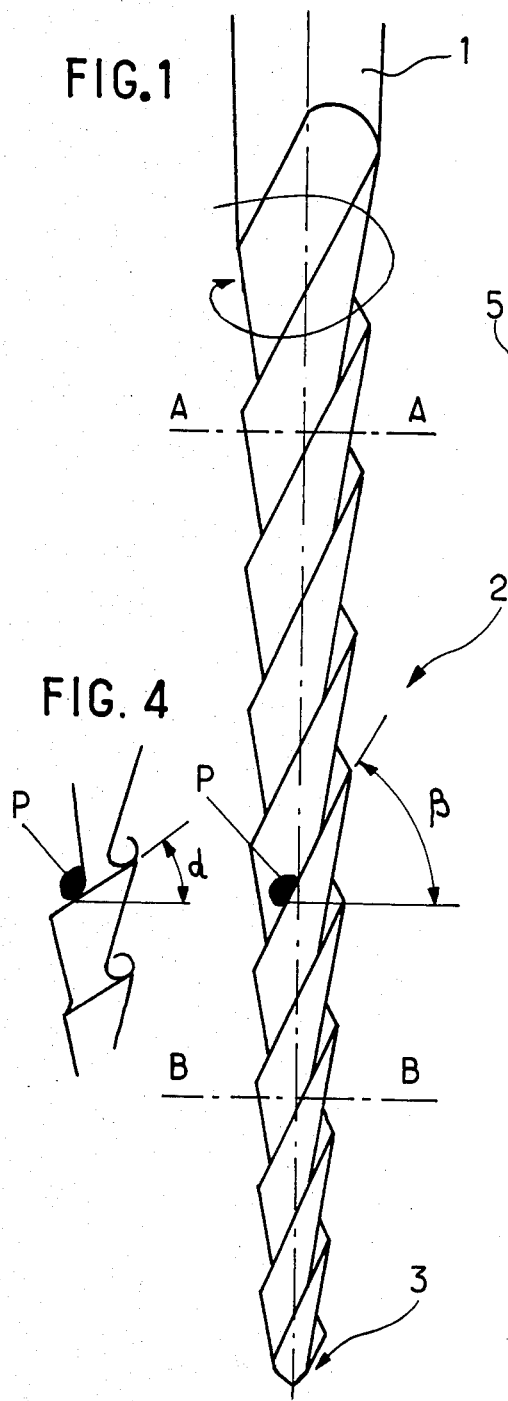
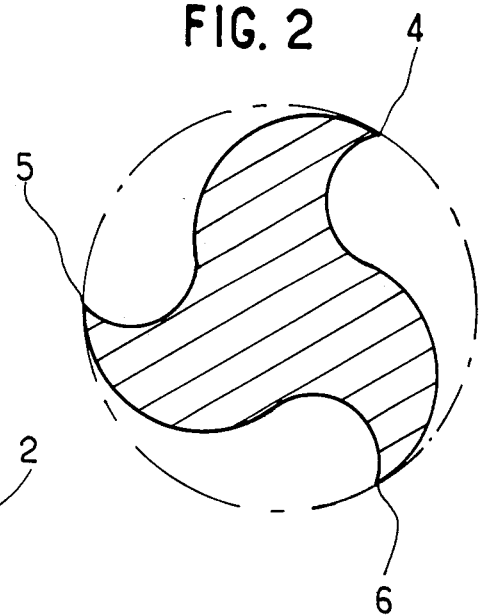
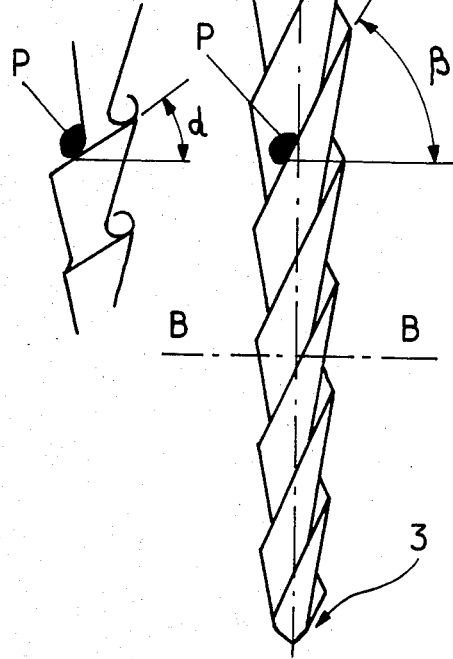
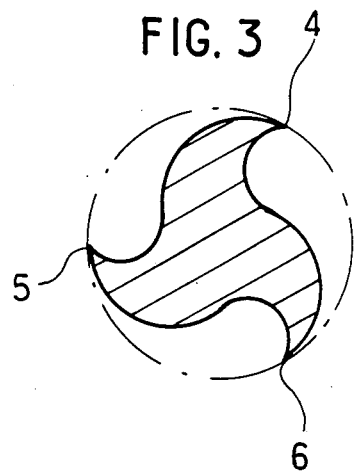

DENTAL DRILL

BACKGROUND OF THE INVENTION

The present invention relates to a dental drill narrowing up to its tip, of the type comprising helicoidal flutes exhibiting on their edges cutting lips for the drilling of the dental canals.

Dental drills with one helicoidal flute have been known for a long time.

Dental drills with two helicoidal flutes have been described, for example, in French Patent Application No. 80.20893.

The drills described in that application exhibit particularly the disadvantage that, in a flattened canal, there is a danger of the tip slipping to the side.

On the other hand, these drills are of constant pitch, which gives them excessive rigidity.

Since moreover the drills of this type are intended to be mounted on a dentistry tool imparting to them an alternating rotary movement of approximately one quarter turn, the drilling executed with a drill with one or two flutes will be inadequate or imperfect because the drill will have a tendency to screw into the asperities of the canal.

SUMMARY OF THE INVENTION

According to the invention, it has been discovered unexpectedly that these disadvantages could be overcome by providing a drill with triple flute with a progressive pitch.

Consequently the invention relates to a dental drill narrowing up to its tip, of the type comprising helicoidal grooves exhibiting on their edges cutting lips for the drilling of the dental canals, characterised in that it comprises a triple helicoidal flute of progressive pitch, so that the free spaces between the cutting lips increase progressively as one moves away from the tip of the drill towards its shank.

BRIEF DESCRIPTION OF THE DRAWINGS

The invention will be better understood from the following description of a preferred embodiment, with reference to the accompanying drawings, wherein:

FIG. 1 is a view in partial side elevation of a dental drill according to the invention;

FIG. 2 is a section along A—A of FIG. 1;

FIG. 3 is a section along B—B of FIG. 1;

FIG. 4 illustrates comparatively the schematic function of a drill with a single flute.

DESCRIPTION OF THE PREFERRED EMBODIMENTS

As is conventional, the drill comprises a shank (1) and a rod (2) terminating in a tip (3).

According to the invention, the rod (2) comprises a triple helicoidal flute (4, 5, 6) illustrated in FIGS. 2 and 3, which also exhibits a progressive pitch.

By virtue of this cutting of the rod into a triple-fluted screwthread, the tip centres itself perfectly in the canal to be drilled, even if the latter is flattened.

On the other hand, the progressive pitch causes the free spaces between the cutting lips to be progressively larger as one moves away from the tip (3). This arrangement causes the central core of the rod (2) itself to consist of a conical rod, but this cone is less pronounced than that generated by the summit of the lips.

This results in greater flexibility of the drill. Since the free spaces between the cutting lips increase towards the shank (1), the free volumes thus determined likewise increase, which facilitates the evacuation of the debris resulting from the drilling, this effect being reinforced by the rotation of the drill.

It is found in practice that the combination of the triple flute with the progressive pitch gives the drills according to the invention remarkable efficacity.

This may be explained by the fact that a three-fluted screwthread is more inclined to the axis of the rod than the thread with one or two flutes.

This is important as a function of the result to be obtained, that is to say a drilling.

Indeed, let us imagine a canal comprising an obstacle such as a projection P formed by a calcification on the wall of the canal (see FIGS. 1 and 4). With a single-fluted drill such as illustrated in FIG. 4, the lip will attack the projection P at a small angle alpha during the rotation of the drill by a half or one turn.

The drill according to the invention, on the other hand, will attack this same projection P at a much larger angle beta, the angles alpha and beta being determined by the tangent at the point P to the thread of the flute which attacks that point, and by the transverse plane perpendicular to the axis of the rod and passing through the point P.

This explains the fact that the prior art drills have a tendency to screw into the canal, whereas that according to the invention will perform its drilling work more easily on the projection P. This effect is reinforced by the use of the drills on instruments imparting to them an alternating rotary movement of approximately one quarter turn, for which it is preferable that the asperities should be attacked frontally, that is to say with the largest possible angle beta.

I claim:

1. A dental drill comprising a tip at one end and a shank at another end thereof, a core of the drill defining a conical rod having conical triple flutes disposed helicoidally axially from the shank to the tip progressively decreasing in diameter and pitch from the shank to the tip, the flutes defining therebetween axial helicoidal grooves, the flutes having cutting lips along peripheral edges thereof for drilling dental canals, and triple flutes at each cross section of the drill the corresponding triple flutes at a corresponding cross section having a same cross sectional configuration.

2. A dental drill according to claim 1, in which said grooves define open spaces between next adjacent flutes disposed in same cross sectional planes, and said open spaces increase in cross section free volume in a direction axially toward the shank.

* * * * *